(12) United States Patent
Li

(10) Patent No.: US 8,097,134 B2
(45) Date of Patent: Jan. 17, 2012

(54) ADDRESSABLE CHEM/BIO CHIP ARRAY

(75) Inventor: Changming Li, Singapore (SG)

(73) Assignee: Nanyang Technological University, Singapore (SG)

( * ) Notice: Subject to any disclaimer, the term of this patent is extended or adjusted under 35 U.S.C. 154(b) by 1357 days.

(21) Appl. No.: 11/097,945

(22) Filed: Apr. 1, 2005

(65) Prior Publication Data

US 2005/0252777 A1 Nov. 17, 2005

Related U.S. Application Data

(60) Provisional application No. 60/558,115, filed on Apr. 1, 2004.

(51) Int. Cl.
*G01N 27/26* (2006.01)

(52) U.S. Cl. .................................. 204/403.01; 204/267

(58) Field of Classification Search .................. 204/600, 204/400, 403.01, 267; 205/775
See application file for complete search history.

(56) References Cited

U.S. PATENT DOCUMENTS

| | | | |
|---|---|---|---|
| 4,072,576 A | 2/1978 | Arwin et al. | |
| 4,098,645 A | 7/1978 | Hartdegen et al. | |
| 4,414,323 A | 11/1983 | Masuda | |
| 4,840,893 A | 6/1989 | Hill et al. | |
| 5,164,319 A | 11/1992 | Hafeman et al. | |
| 5,187,096 A | 2/1993 | Giaever et al. | |
| 5,202,261 A | 4/1993 | Musho et al. | |
| 5,403,451 A | 4/1995 | Riviello et al. | |
| 5,532,128 A | 7/1996 | Eggers et al. | |
| 5,653,989 A | 8/1997 | Sattler | |
| 5,670,322 A | 9/1997 | Eggers et al. | |
| 5,891,630 A | 4/1999 | Eggers et al. | |
| 5,942,692 A * | 8/1999 | Haase et al. ..................... 73/724 |
| 6,602,400 B1 * | 8/2003 | Choong et al. ..................... 506/9 |
| 2002/0051975 A1 | 5/2002 | Li et al. | |
| 2002/0090649 A1 | 7/2002 | Chan | |
| 2002/0160427 A1 | 10/2002 | Beier et al. | |
| 2003/0138845 A1 | 7/2003 | Li et al. | |
| 2003/0209432 A1 | 11/2003 | Choong et al. | |

FOREIGN PATENT DOCUMENTS

| | | |
|---|---|---|
| WO | 9306237 | 9/1992 |
| WO | 0077523 | 12/2000 |
| WO | 0142508 | 6/2001 |
| WO | 0157533 | 8/2001 |
| WO | 0161053 | 8/2001 |
| WO | 03010338 | 2/2003 |

OTHER PUBLICATIONS

L.G. Mendoza et al., "High-Throughput Microarray-Based Enzyme-Linked Immunoabsorbent Assay (ELISA)," BioTechniques, 1999, pp. 778-788, vol. 27, issue 4. Ying Ding et al., "Feasability Studies of Simulatneous Multianalyte Amperometric Immunoassay Based on Spatial Resolution," Journal Pharmaceutical and Biomedical Analysis, 1999, pp. 153-161, vol. 19, issues 1-2.
J.H. Ng et al., "Biomedical Applications of Protein Chips," Journal of Cellular and Molecular Medicine, 2002, pp. 329-340, vol. 6, issue 3.
S. Purushothama et al., "Small Volume Bead Assay for Ovalbumin with Electrochemical Detection," Analyst, 2001, pp. 337-341, vol. 126.

* cited by examiner

*Primary Examiner* — Jeffrey T Barton
*Assistant Examiner* — J. Christopher Ball
(74) *Attorney, Agent, or Firm* — Dinsmore & Shohl LLP

(57) ABSTRACT

Addressable bio/chem chips include a plurality of isolated test cells, each addressable by at least two electrodes for measuring electrical characteristics of probe/test molecule interactions. In one embodiment, electrodes are located within a channel to allow for four terminal measurement. In another embodiment, electrodes are arranged in rows and columns and interconnected with electrolyte pads used as test sites. In yet another embodiment, electrodes are arranged in cells, with each cell including a counter electrode surrounded encircled by working electrodes.

21 Claims, 8 Drawing Sheets

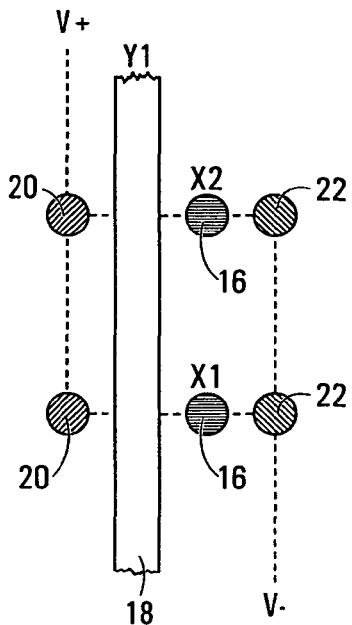
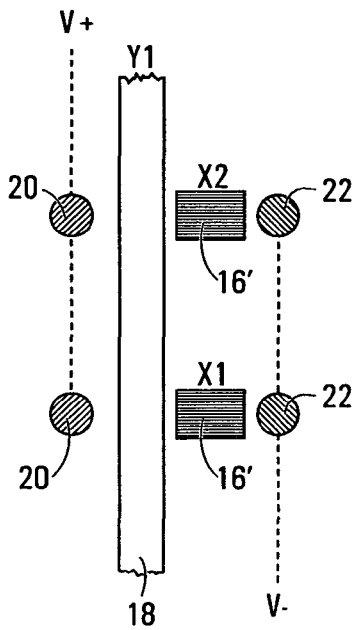
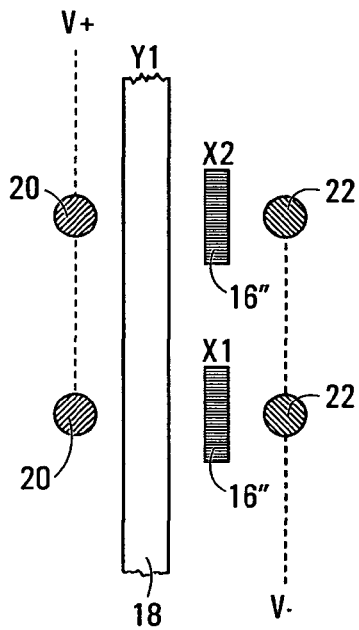
FIG. 2A  FIG. 2B  FIG. 2C
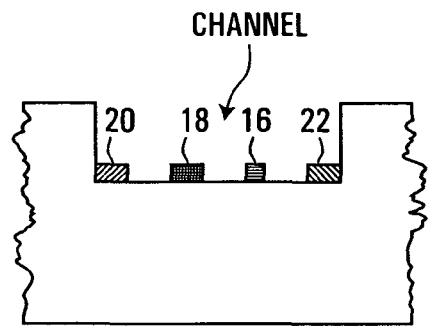
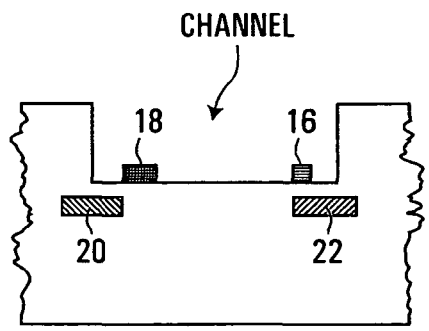
FIG. 3A  FIG. 3B

ADDRESSABLE CHEM/BIO CHIP ARRAY

CROSS-REFERENCE TO RELATED APPLICATIONS

This application claims benefits from U.S. Provisional Patent Application No. 60/558,115, filed Apr. 1, 2004, the contents of which are hereby incorporated herein by reference.

FIELD OF THE INVENTION

The present invention relates generally to the electronic or electrochemical detection of bio- and chemical molecules, and more particularly to arrays used in such detection.

BACKGROUND OF THE INVENTION

Methods for electrical or electrochemical detection of molecular interactions between biomolecules have provided an attractive alternative to detection techniques relying on radioactive or fluorescent labels. Electrical and electrochemical detection techniques are based on the detection of alterations in the electrical properties of an electrode arising from interactions between molecules attached to the surface of the electrode (often referred to as "probe" molecules) and molecules present in a reaction mixture (often referred to as "target" molecules) in contact with the electrode. Examples of methods and devices related to electrical or electrochemical detection of biomolecules are disclosed in U.S. Pat. Nos. 4,072,576, 4,098,645, 4,414,323, 4,840,893, 5,164,319, 5,187,096, and 5,891,630.

Electrical or electrochemical detection eliminates many of the disadvantages inherent in the use of radioactive or fluorescent labels to detect interactions between probe and target molecules. Electrical or electrochemical detection is safe, inexpensive, sensitive, and is not burdened with complex and onerous regulatory requirements. The development of microfabricated arrays (microarrays) of bio- and chemical molecules has led to further improvements of traditional analytical techniques. Microarrays of bio- and molecules (e.g. oligonucleotides, nucleic acids, proteins, peptides, or antibodies) have utility in a wide variety of applications in which molecular interactions between target molecules in a reaction mixture and large numbers of distinct probe molecules bound to defined regions of a substrate can be simultaneously assayed using electrical, optical, or radioactive detection strategies. Microarrays address the demands for inexpensive, high-throughput detection of biomolecular interactions. Obviously, microarrays can also provide a low cost and high-throughput platform for detection of chemical species. There are, however, problems associated with electrical or electronic systems as such devices cannot detect the same way as optical scanners do and require multiplexing to scan different detection spots. Electronic detection systems also require an electrolyte (either solid or liquid), making ionic isolation of different detection spots critical.

Although biochip arrays for the electrochemical detection of molecular interactions between bio- and/or chemical molecules have been proposed, these devices have significant disadvantages. For example, the device disclosed by Egger et al. in U.S. Pat. Nos. 5,670,322 and 5,532,128 cannot be made column-and-row (or "x-y") addressable, thus limiting the density of the test sites in the array and the usefulness of the apparatus. In U.S. Pat. No. 5,653,939, Hollis et al. disclosed an x-y addressable array wherein a solid supporting substrate comprises a plurality of test sites in electrochemical contact with a set of orthogonally oriented electrodes. However, Hollis et al. does not provide an apparatus for eliminating the ionic shortage when an electrolyte is applied in microarray chips, in which case, the array electrodes cannot be addressed.

US Patent Application No. 20020090649A1 discloses a high density addressable array for electronic detection biochips. The array, however, does not provide for true four-terminal electronic detection for high S/N ratio and high sensitivity, and does not lend itself for use in high density array chips without isolation channels.

Impedance measurements could be used to directly detect the impedance changes after biomolecular interaction. Most protein and DNA sensors require labelling (such as florescent labels) to report biomolecular interactions. Impedance can enable label-less detection. However, the sensitivity needs to be further improved.

Electronic or electrochemical sensors require two electrodes (working and counter/reference electrodes) or three electrodes (working, counter and reference electrodes) for detection measurements. Existing electronic array sensors are designed to have either two or three electrodes at every array detection site, or are designed to have common counter or reference electrodes. Two or three electrodes per test site typically results in many electrodes and high manufacturing cost. Common counter or reference electrodes cause different solution resistance resulting in additional noise and difficult data processing.

There thus remains a need for an improved column-and-row addressable chem/bio chip array for the electrical or electrochemical detection of molecular interactions that are effective while reducing the cost of performing various analyses, and that can also be easily and cost effectively fabricated. Such devices, and methods for their use, may have wide application in the fields of medicine and genetics and molecular biology research.

SUMMARY OF THE INVENTION

In accordance with the present invention, addressable bio/chem chips include a plurality of isolated test cells or regions, each addressable by at least two electrodes for measuring electrical characteristics of probe/test molecule interactions. In one embodiment, electrodes are located within a channel to allow for four terminal measurement. In another embodiment, electrodes are arranged in rows and columns and interconnected with electrolyte pads used as test sites. In yet another embodiment, electrodes are arranged in cells, with each cell including a counter electrode surrounded encircled by working electrodes.

In accordance with an aspect of the present invention, there is provided a column-and-row addressable chip including a substrate, a plurality of channels formed in the substrate, a plurality of column electrodes, each one of the plurality extending along a length of one of the channels, a plurality of spaced row electrodes, within each of the channels and electrically isolated from the column electrode of the channel, and at least one pair of electrodes for interconnection with a voltage source, electrically isolated from the row and column electrodes, and positioned to generate a widthwise potential across at least a portion of one of the channels.

In accordance with an aspect of the present invention, there is provided an addressable chip including a substrate having a planar surface, a plurality of row electrodes formed atop the planar surface, a plurality of column electrodes, each formed atop the planar surface proximate a row electrode and electrically isolated from the row electrodes; electrolyte pads covering each of the column electrodes, proximate a row electrode; pairs of the row and column electrodes for interconnection with a voltage source, to generate a potential for detection of chem/biological probe and target molecule interaction proximate the electrolyte pads. Portions of the planar surface not covered by the pads are hydrophobic.

In accordance with an aspect of the present invention, there is provided an addressable chip including: a substrate; a plurality of counter electrodes formed on the substrate; a plurality of working electrodes, groups of the plurality of working electrodes encircling each of the plurality of counter electrodes and electrically isolated from the counter electrodes; pairs of the counter/working electrodes for interconnection with a voltage source, to generate a potential for detection of chem/biological probe and target molecule interaction proximate a pair of counter/working electrodes.

In accordance with another aspect of the invention, there is provided a test apparatus including a substrate, a plurality of pads formed of insoluble material for binding to samples of interest, arranged on the substrate; a plurality of working electrodes, each of the plurality of working electrodes electrically interconnected to first groups of the plurality of pads; a plurality of counter electrodes, each of the plurality of counter electrodes electrically interconnected to second groups of the plurality of pads; wherein each of the pads is interconnected to one of the plurality of working electrodes and one of the plurality of counter electrodes; a measuring device for measuring electrical characteristics at a selected pair of the counter and working electrodes, to analyse an analyte proximate the one of the plurality of pads interconnected with the selected pair of the counter and working electrodes.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures which illustrate by way of example only, embodiments of the present invention.

FIG. 2 is a top schematic view of a portion of bio/chem chip array of FIG. 1;

FIG. 3A is a partial cross-sectional view of bio/chem chip array of FIG. 1;

FIG. 3B is a partial cross-sectional view of bio/chem chip exemplary of another embodiment of the present invention;

DETAILED DESCRIPTION

Figure 1:
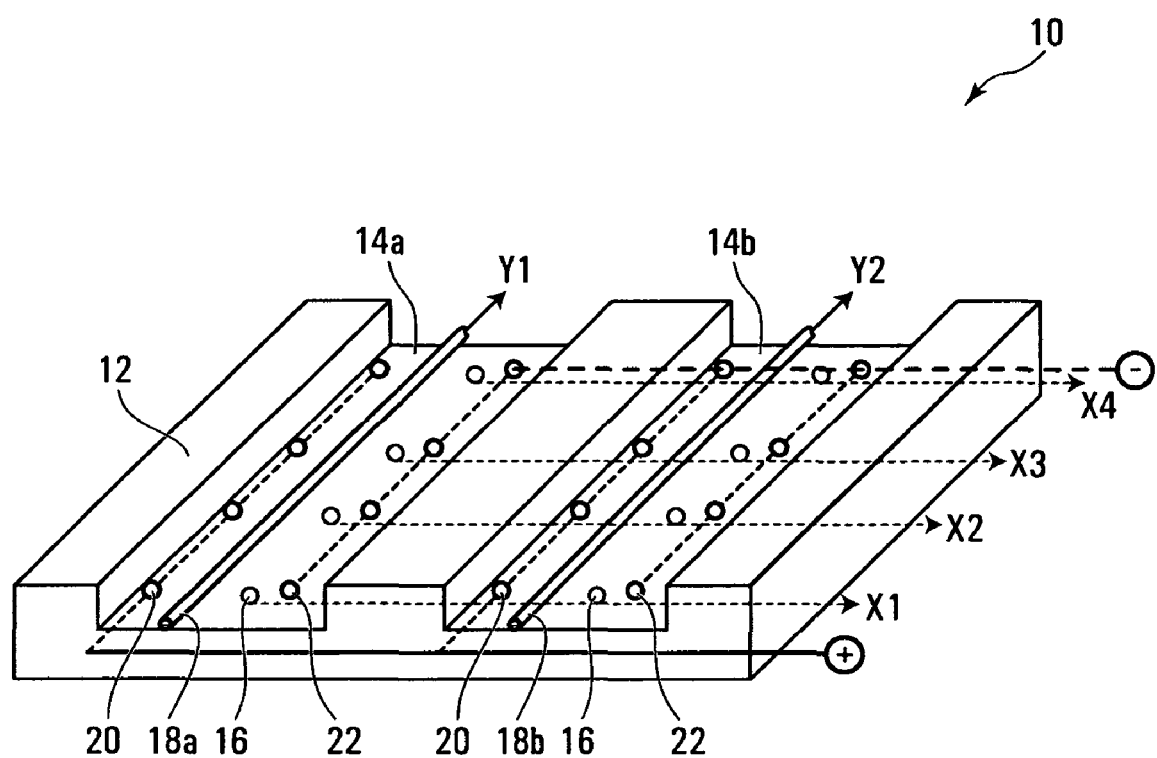
FIG. 1 is a perspective view of a bio/chem chip array, exemplary of an embodiment of the present invention.

FIG. 1 schematically illustrates a four-terminal addressable bio/chem chip array 10, exemplary of an embodiment of the present invention.

As illustrated, array 10 includes a substrate 12, and plurality of width wise extending microchannels 14a and 14b (individually and collectively microchannels 14). Substrate 12 is formed of an insulating material such as plastic, ceramic, glass, rubber, fabric, printed circuit board, silicon or combinations thereof. Microchannels 14 are formed in the top surface of substrate 12. Example microchannels 14 may be formed using conventional etching or embossing techniques, and may have widths on the order of 0.1 μm to 2000 μm and depths of 0.1 to 2000 μm. For clarity, depicted array 10 only includes two microchannels 14a and 14b. However, a suitably sized substrate 12 may include any number of similarly formed microchannels. As well, in the depicted embodiment, microchannels 14 extend from edge to edge of substrate 12. However, microchannels 14 may only extend partially between edges.

Exemplary array 10 further includes x-y addressable row and column electrodes 16, 18 in different microchannels 14, as further illustrated in FIG. 2A. As illustrated, addressable column electrodes 18a, 18b (individually and collectively column electrodes 18) are designed as conductive strips, each one running through the length of microchannels 14. Column electrodes 18 thus provide a relatively large surface area, which can serve as reference/counter electrodes without significant polarization. Addressable row (x) electrodes 16, on the other hand, are formed within each channel and isolated from column electrodes 18. Row and column electrodes 16, 18 are electrically isolated from each other. In the depicted embodiment of FIG. 2A row electrodes 16 are formed as finite sized generally round conductive pads within microchannels 14. Example alternate shapes for row electrodes 16 will be readily apparent to a person of ordinary skill. For example, electrodes 16' and 16" formed as generally rectangular and square conductive pads are depicted in FIGS. 2B and 2C, respectively. Again, for clarity, depicted array 10 only includes four row electrodes 16. A suitably sized substrate 12 may include any number of similarly formed row electrodes 16.

Row electrodes 16 may be provided at spacings on the order of 0.1 μm to 500 μm. Exemplary row/counter electrodes 16, 18 have sizes on the order of 0.001 μm to 500 μm, which can be fabricated by conventional lithography or nanolithography technologies. Examples of the row/column and voltage electrode materials include solid or porous gold, silver, platinum, copper, titanium, chromium, aluminum, metal oxide, metal carbide, carbon, graphite, fullerene, conductive plastic, conductive polymer, metal impregnated polymers, or combinations thereof.

Additionally, pairs of electrodes 20, 22 for imposing an applied voltage (referred to as "voltage electrodes") are located in microchannels 14 outside of the addressable row/column (x/y) electrodes 16, 18. In the depicted embodiment, one of the pair of voltage electrodes 20, 22 is formed on either side of column electrode 18 and on either side of each row electrode 16. All positive voltage electrodes 20 and negative voltage electrodes 22 of array 10 in microchannels 14 may be electronically interconnected together at two lines.

A section view of the row/column electrodes 16, 18 and voltage electrodes 20, 22 which are isolated from the current electrodes for true four-terminal measurements is illustrated in FIG. 3A. As will become apparent, each pair of voltage electrodes 20, 22 provides an electrical field for four-terminal impedance measurements, and are isolated from the x-y addressable electrodes 16, 18.

Since the function of voltage electrodes 20, 22 is to establish an electric field in channel 14, they can be isolated from the channel 14 and testing fluid samples. Thus, alternatively, voltage electrodes 20, 22 can be embedded into substrate 12 as illustrated in FIG. 3B. This design allows conducting four-terminal electrical and addressable detection with high signal to noise (S/N) ratio and simple multiplexing detection for significantly reducing I/O lines.

In the arrangements of both FIGS. 3A and 3B, column electrodes 16 are separated by microchannels 14. As such, as column electrodes are isolated, a pair of arrayed row/column electrodes 16, 18 can be addressed independently, without being influenced or influencing measurements at other pairs of row/column electrodes 16/18.

In operation, different probe molecules or sensing layers such as DNA, proteins, peptides, etc may be immobilized at or proximate row electrodes 16 in microchannels 14 by linkers or other modification methods such as adsorption, covalent binding, chemical affinity, surface monolayer self-assembly, etc.

Samples containing analyte that may contain target molecules is flown into or through channels 14. Optionally, thereafter, the channels may be washed to remove any excess, non-bound analyte.

A voltage is applied across electrodes 20/22, during or after flow of the analyte. This voltage, in turn generates a lateral electric field within each channel between electrodes 20 and 22, and between electrodes 16 and 18. In the presence of immobilized probe molecules bound to target molecules, proximate for example, the $i^{th}$ and $j^{th}$ row and column electrodes 16, 18, current may flow between these $i^{th}$ and $j^{th}$ row and column electrodes 16 and 18. Conventional measuring equipment may detect this current to verify the presence of the immobilized probe molecules and target molecule. Alternatively, impedance changes at the $i^{th}$ and $j^{th}$ row and column electrodes may be detected in other conventional manners. Absent immobilized probe molecule/target molecule combinations, proximate row/column electrode pair 16, 18 no significant current will flow between proximate row and column electrodes 16, 18.

That is, molecular interactions between the immobilized probe molecules and target molecules that bind specifically to the probe molecules may be detected as a difference in the electrical signal detected at the corresponding row and column electrode 16, 18. If a gel or solid electrolyte is applied instead of the liquid electrolyte at these microchannels 14 an addressable array can be fabricated to detect gas compounds.

As will be appreciated, the number of samples that may be independently tested using array 10 equals the number of row electrodes since the column channels are isolated from each other for detection of different samples.

Advantageously exemplary array 10 enables true four-terminal impedance measurements with a high S/N ratio for highly sensitive electronic and electrochemical array sensors. The applied electrical field between pairs of voltage electrodes 20/22 may also enhance the diffusion rates of target biomolecules in analytes if the target molecules are charged. As DNA and many other biomolecules such as proteins are charged molecules, array 10 is particularly useful for biomolecule detection. Conveniently the number of I/O lines for multiplexing is reduced and can conduct different electronic detections. Hydrophobic coating or additional isolation parts are not required. The design may thus result in higher automation performance, shorter assay times and lower manufacturing costs.

Figure 4A:
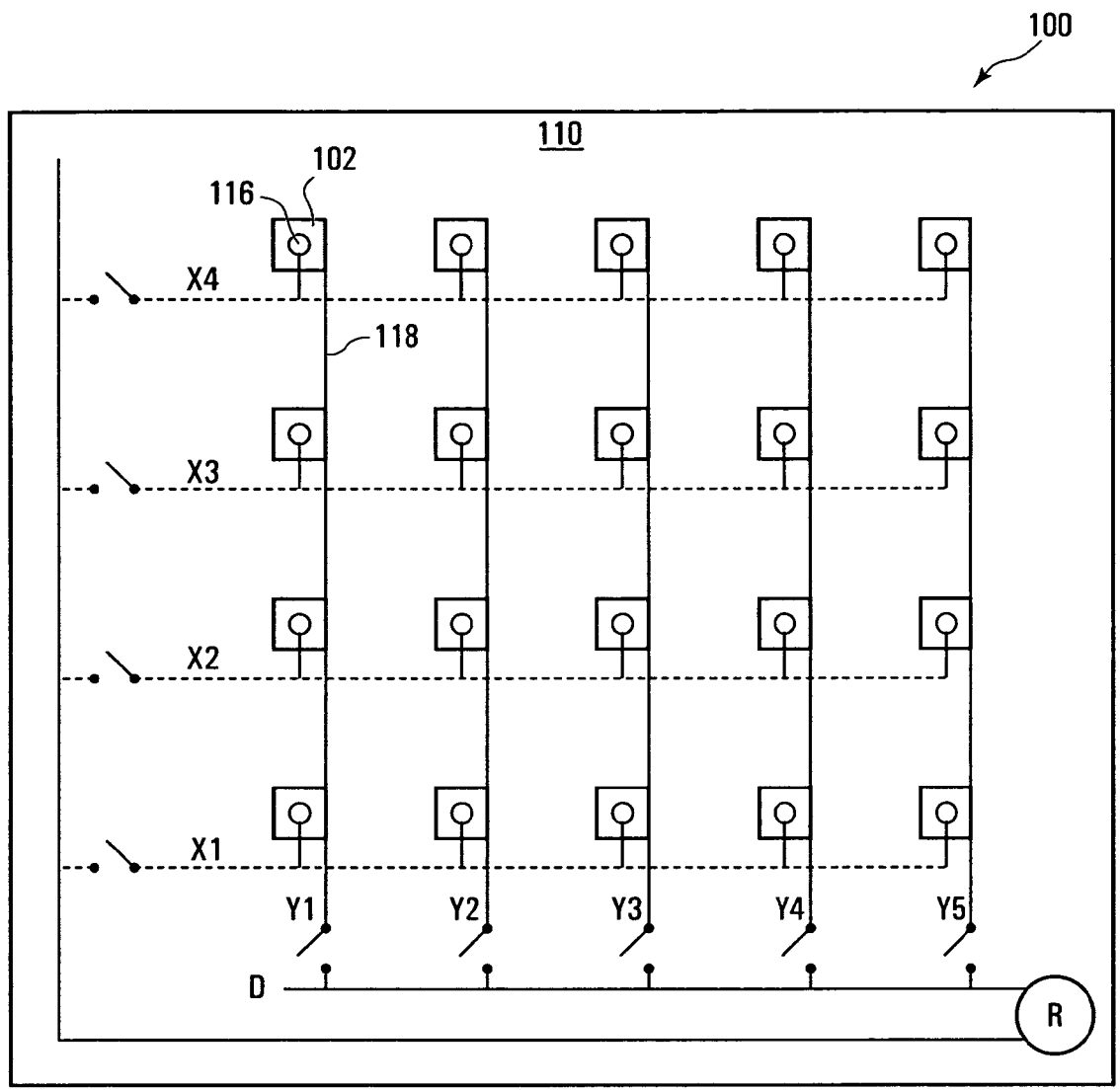
FIGS. 4A and 4B are schematic diagrams of a bio/chem chip array, exemplary of another embodiment of the present invention.

FIG. 4A schematically illustrates an alternate addressable chem/bio chip array 100 for use as an electronic chem/bio-chip in test apparatus 99. Array 100 includes a substrate 110 having a generally planar surface and an array of row and column electrodes 116 formed thereon. Substrate 110 may be hydrophobic, or coated with a hydrophobic coating. An insoluble layer, for example, in the form of solid, semi-solid or polymer electrolyte pads 102 is coated on top of each electrode 116 for formation of a test cell. In this embodiment, each electrolyte pad 102 further covers a proximate column electrode 118.

Pads 102 may be used to attach probe molecules. Pads 102 may, for example, be formed of cross-linked hydrogel, and can be formed by printing or dispensing. Alternatively pads 102 may be formed of polyacrylamide on pairs of row/column electrodes followed by the deposition of a mixture solution of monomer acrylamide and streptavidin only onto the arrayed row electrode. After UV-curing, the streptavidin molecules are entrapped in the polymerized polymer matrix and can be used to attach any biotinylated probe. A monomer with functional groups such amine or hydroxyl groups for protein probe attachment can also be used. Alternatively, the electrolyte pad 102 may be formed after probe attachment on top of pairs of row/column electrode.

Pads 102 can be used in both gas or liquid sample detection. After incubation of samples on pads 102, excess liquid will flow out. Different arrayed cells are isolated by hydrophobic plastic substrates.

Conveniently, array 100 may be easily and inexpensively manufactured and reduced numbers of I/O lines are required due to the addressable array. Conveniently, insoluble pads 102 when formed of a polymer electrolyte provide a bioconjugation platform for the attachment of different biomolecular probes for the detection of target molecules, such as proteins, DNA and peptides. Different or like probe molecules may be attached at each pad 102, as desired.

As will be appreciated, arrangement of row and column electrodes 116, 118 and pads 102 need not be strictly Cartesian. Instead, rows and columns may arranged in numerous ways, with row electrodes and column electrodes interconnected to groups of pads 102, with each pad 102 interconnected with a unique electrode pair.

Figure 5A:
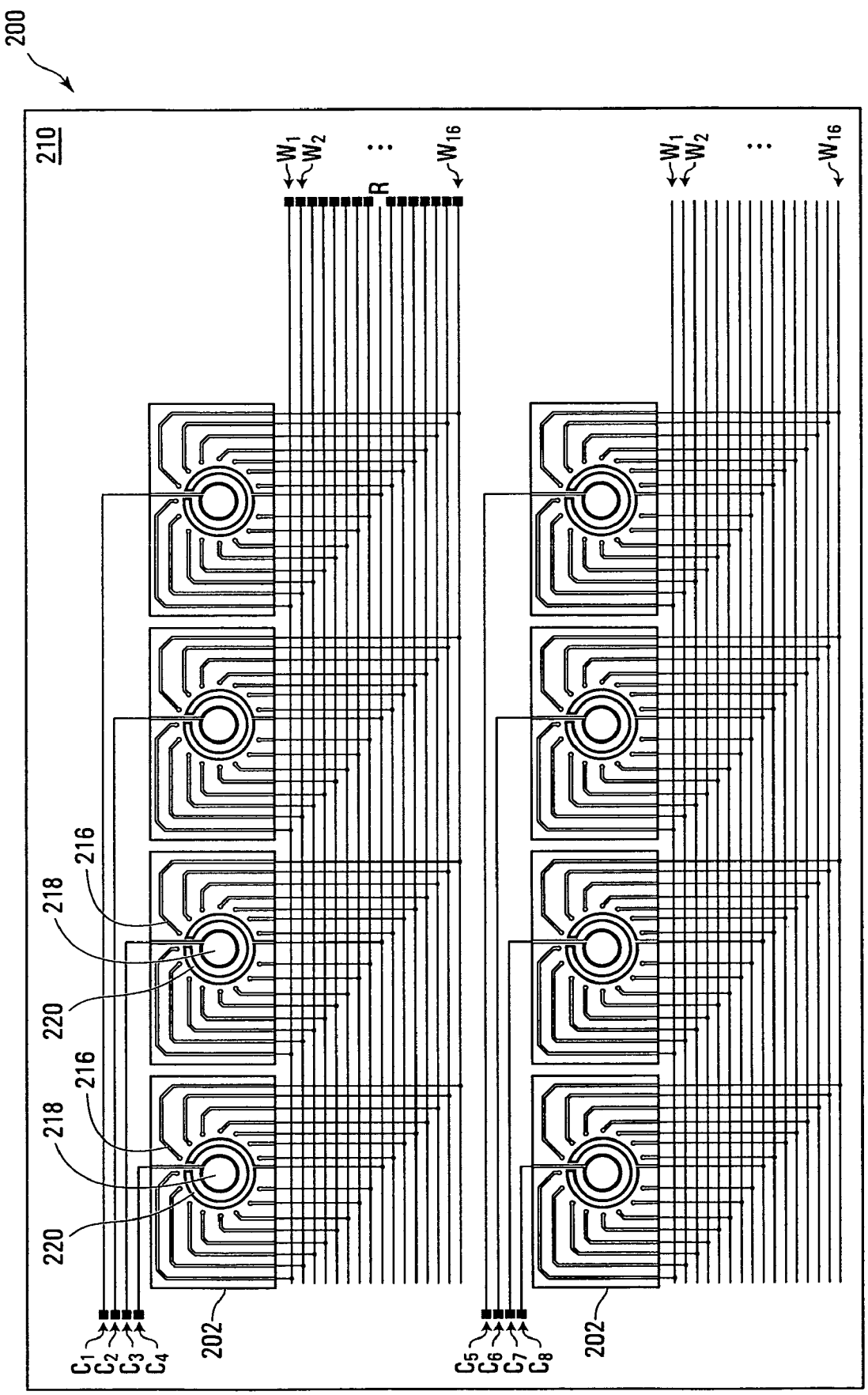
FIG. 5A is a schematic diagram of a bio/chem chip array, exemplary of another embodiment of the present invention.
Figure 5B:
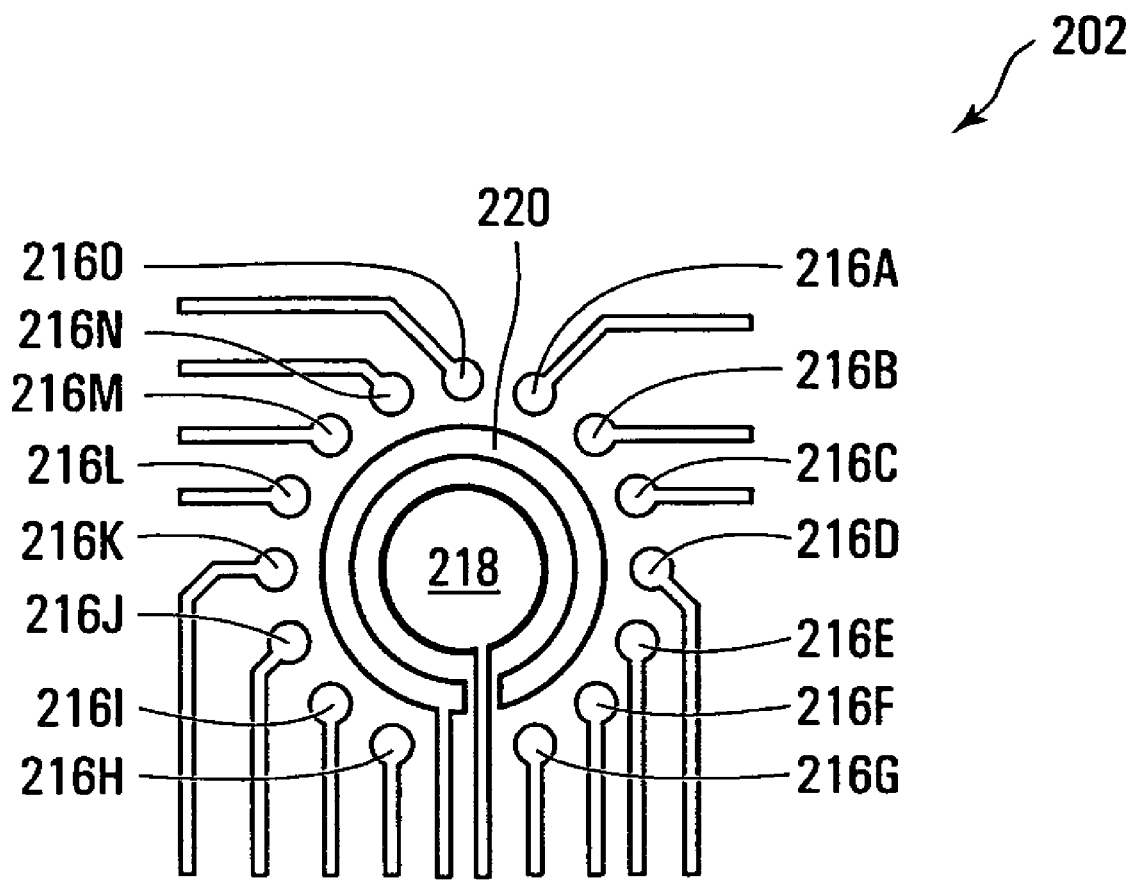
FIG. 5B is an enlarged view of the counter-working electrode addressable chip of FIG. 5A.

In an alternate embodiment depicted in FIGS. 5A and 5B, an addressable bio/chem chip 200 is arranged as a plurality of working/counter electrode complexes 202. Each working/counter electrode complex 202 includes a single counter electrode 218 surrounded by a group of working electrodes 216, as best illustrated in FIG. 5B. Each group includes a plurality of working electrodes 216a, 216b . . . (individually and collectively working electrodes 216). Optional reference electrode 220 may further surround each counter electrode 218. In the depicted embodiment, the working electrodes 216 form a partial circle about each counter electrode. Each counter/working electrode pair 218/216 can be uniquely addressed by a single counter electrode 218 $C_i$ and a single working electrode 216 $W_n$. For example, $C_1 W_5$ addresses a detection at working electrode 5 of counter electrode 1. Conveniently, like positioned working electrodes of all working/counter electrode complexes 202 may be interconnected, as best illustrated in FIG. 5A.

In order to allow independent assays at the various working/electrode complexes 202, complexes 202 may be physically isolated by one or more upstanding walls or trenches separating each complex 202 from each other complex 202. Channels (not shown) may also be formed in a substrate 210 to guide liquid analyte to each complex 202. Alternatively, a solid or semi-solid electrolyte pad (not shown) can be formed on various working/electrode complexes 202, respectively, and complexes 202 may be isolated from each other by hydrophobic surface between two neighboured complexes.

Again, any portions of the top surface of the surface of chip 200 not covered by complexes 202 may be covered, or formed of a hydrophobic substance or layer.

Probe molecules may be immobilized proximate the tip of each working electrode

Chip 200, like addressable chip 100, can significantly reduce the number of I/O lines required for simpler multiplex measurements and thus result in low manufacturing costs. Conveniently, due to the symmetric arrangement of working electrodes 216 about counter electrodes 218, the electrical background contributions at each working/counter electrode pair 216/218, such as electrolyte resistance, distribution electronic components, etc. from different detection sites proximate a single counter electrode 218 are identical to each other. This can significantly improve the S/N ratio of measured signals. In addition, every group of working electrodes 216 about a single counter electrode 218 can be used to detect different samples and each working electrode 216 may detect a different target biomolecules for more flexibility. Each working electrode 216, in turn, can be immobilized with a unique probe molecule.

Addressable chip 200 may be fabricated using conventional printed circuit board technology on a plastic substrate. In the depicted embodiment, generally round working and counter electrodes 216, 218 and interconnects are etched in conductive material atop a substrate 210. Substrate 210 may be of the same material as substrate 104. Numerous other configurations and fabrication techniques will be understood by persons for ordinary skill. For example, electrodes 216, 218 may be generally round, square, rectangular or the like. A suitable biochip 200 may be formed using lithography and ceramic, and the substrate materials can be plastic, ceramic, silicon and the like. Working and counter electrodes may be formed of at least one of platinum, gold, metal, carbon, carbides, nitrides, conductive polymers.

In operation, array 100 (or array 200) is first incubated with test samples and then washed. Remaining water is removed from the hydrophobic surface, not covered by insoluble pads 102. Since this surface is hydrophobic, water can easily be removed. Thus, array 100 (or array 200) can be treated as a free-standing component for electronic detection without the problem of cross assay interference, since every detection site forms a miniaturized isolated test location, addressable by two electrodes.

Once array has been incubated in the test samples and washed, array 100 (or 200) may be used together with impedance spectroscopy to detect bio-molecule binding, such as DNA matching and protein bindings, proximate each addressed row and column electrode pair 116, 118, or counter/working electrode pair 216, 218. In such applications, the binding behavior of target molecules causes changes of the solution-electrode interface impedance. By characterizing the impedance spectrum, binding can be detected.

Figure 6A:
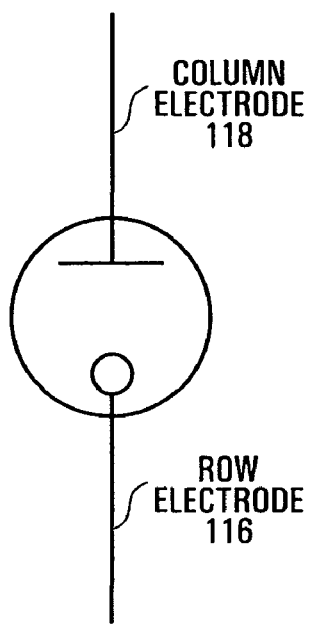
FIGS. 6A and 6B are schematic diagrams of test cells of the bio/chem chip array of FIGS. 4A and 4B.
Figure 6B:
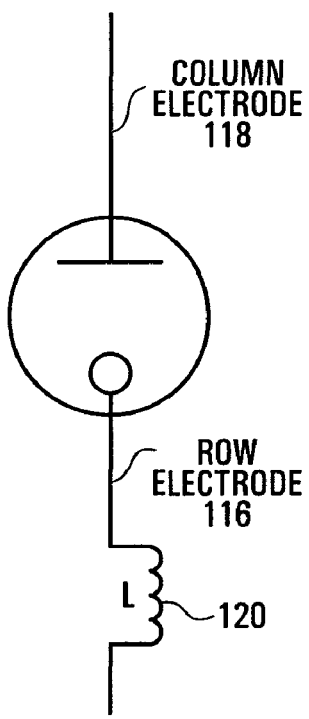

That is, each addressed row/column electrode pair 116, 118 of array 100 (FIG. 4A) may be modelled as a two-electrode test cell as shown in FIGS. 6A and 6B. Counter/working electrode pair 216, 218 of array 200 (FIG. 5A) may be similarly modelled. The interface between the bound test sample and the row electrode 116 may be modelled as a double-layer structure. Now, the impedance between the most proximate row and column electrodes 116, 118, as a function of frequency (w) of any applied voltage, can be expressed as $$Z = R - j\frac{1}{\omega C} \quad (1)$$

where R is resistance, and C is the capacitance between the row/column electrode 116, 118. As will be appreciated, there is no material inductance term in the impedance expression for the double-layer structure, and the imaginary part is always available.

When this test cell is used to detect molecule binding, the relative sensitivity is usually characterized by the dependence of the relative change of the resistance, $(R-R_0)/R_0$, on the target molecule concentration, where $R_0$ is the electrode-solution interface resistance when no binding takes place, and R is the electrode-solution interface resistance in the presence of binding. Bio/chemical molecule interaction on an electrode surface also results in change of the double-layer capacitance. The relative change of double layer capacitance, $(C-C_0)/C_0$ electrode can be used for target bio/chemical molecule detection.

Figure 4B:
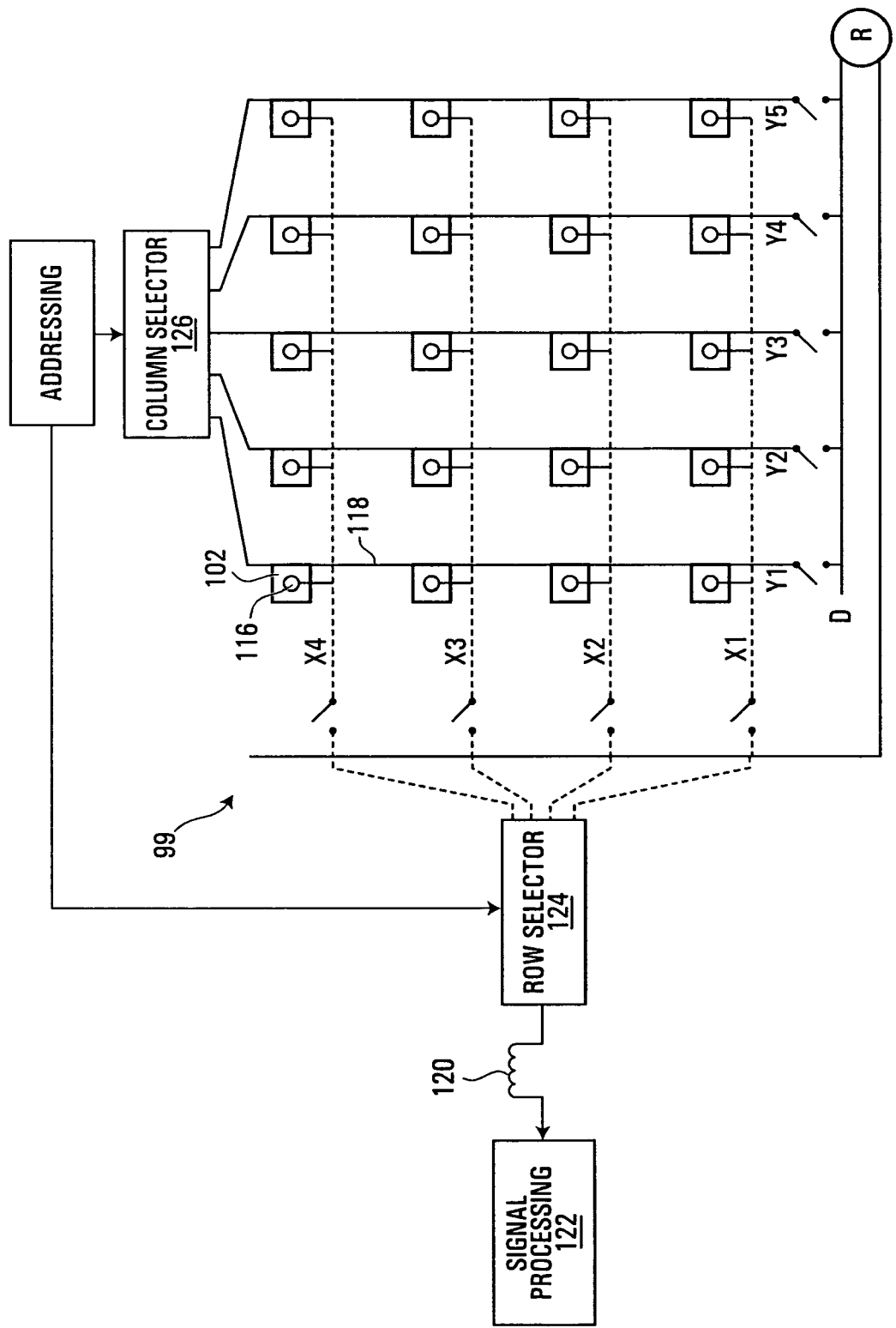

However, sensitivity may be improved if an inductor is put in series with the row or column electrode 116, 118, as depicted in FIGS. 4B and 6B, or counter/working electrode 216, 218. The sensitivity of this test cell may be calculated as $[d(|Z-Z_0|)/d\log(f)]/[d|Z_0|/d\log(f)]$. Here, $Z_0$ is the impedance of the electrode-solution interface and the inductor when no binding takes place, Z is the impedance of the electrode-solution interface and the inductor when binding takes place, and f is frequency.

Figure 7:
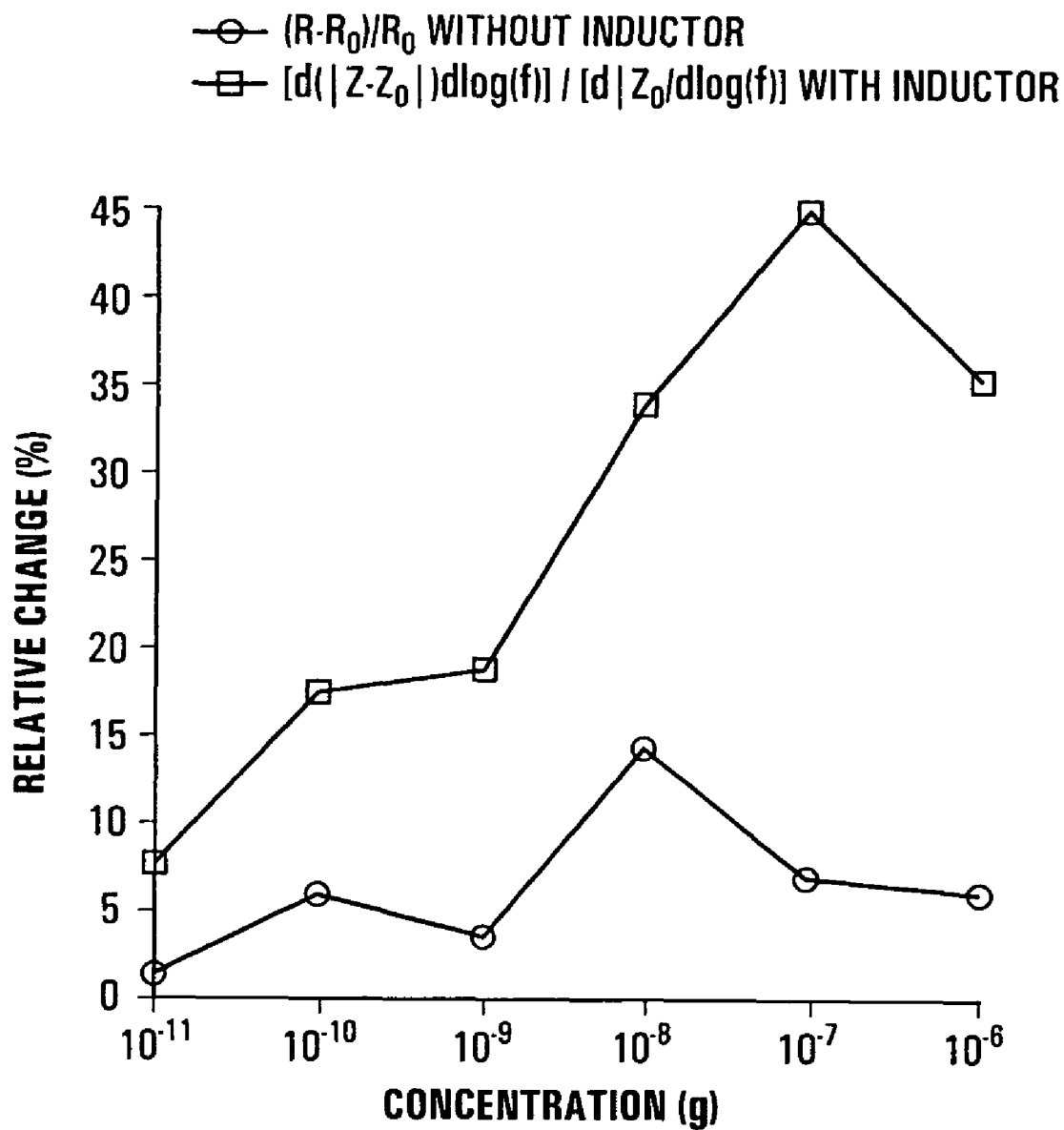
FIG. 7 is a graph illustrating the sensitivity of test cells of the bio/chem chip arrays of FIGS. 4A and 4B.

FIG. 7 illustrates the relative sensitivity of a test cell of array 100 in the presence of inductor 120 (FIG. 6B), and in the absence of inductor 120 (FIG. 6A), using the same analyte (the binding effect of chicken antigen to antibody), for various concentrations of the analyte. It is evident that the relative impedance amplitude change of the row/column electrodes in the presence of an inductor is much higher than the relative resistance change of the system without inductor, and both the results are correlated with each other.

After addition of an inductor, L, the impedance between row and column electrodes 116, 118 will be $$Z = R - j\frac{1}{\omega C} + j\omega L = R + j\left(\omega L - \frac{1}{\omega C}\right) \quad (2)$$

Thus, there is a specific resonant frequency, $f_0$, at which Z approaches the minimum value of R, and $[d(|Z-Z_0|)/d\log(f)]/[d|Z_0|/d\log(f)]$ at $f_0$ will approach to ∞. A measurement frequency, f can be selected to very close to $f_0$ and to have very small $\Delta f = f - f_0$. Since $[d(|Z-Z_0|)/d\log(f)]/[d|Z_0|/d\log(f)]$ value can be extremely large when f approaches to $f_0$, the capacitance component change in the impedance (inductance is fixed) from target and probe molecule bindings or interactions is significantly amplified at a measurement frequency close to $f_0$. Thus, this method can be significantly increased the measurement sensitivity.

As such, as illustrated in FIG. 4B, an addressable array 100 forms part of a test apparatus 99. A single inductor 120 interconnects a measuring device 122 to selected pairs of row/column electrodes 116, 118 proximate pads 102. Example measuring device 122 may, for example, take the form of a conventional impedance frequency analyser, and may include a variable frequency voltage source and an ammeter (not shown). Row/column selectors 124 and 126 may control which row/column electrode pair 116, 118 is intereconnected with measuring device 122 at any instance in time.

Row/column selectors 124 and 126 may then be operated to interconnect measuring device 122 to each row/column pair 116, 118. For each row/column pair 116, 118 measuring device 122 may be interconnected to that row/column pair 116, 118 and cycled through a range of frequencies to determine the impedance of the row/column pair 116, 118 as a function of frequency. The resulting impedance of each row/column electrode pair 116, 118 may be measured using measuring device 122, to determine the frequency response of the row/column electrode in the presence of a test solution. Alternatively, changes in impedance at or near $f_0$ may be measured for each row/column electrode pair 116, 118. Operation of row/column selectors 124 and 126 and measuring device 122 may be controlled by a general purpose computing device under software control, in manners understood by those of ordinary skill. Results may be tabulated, displayed and/or further processed.

As well, use of exemplary arrays 10, 100, 200 is not limited to detection of biomolecule interactions; it can, for example, also be also used for detection of chemical analytes. The exemplary arrays 10, 100, 200 may be suitable for a variety of applications including for example diagnostics, drug discovery, pathogen detection, food sensing and environmental protection. The arrays 10, 100, 200 can be used to detect molecular interactions such as nucleic acid hybridization, protein binding and other chemical/electrochemical reactions.

EXAMPLE 1

Electrode preparation using array 100 (FIG. 4B): A solution containing 0.1 M pyrrole, purchased from Aldrich), +PBS buffer was prepared as solution A. A solution for probe synthesis was prepared by adding 1 μl of anti-AZT, 281 D, thymidine analog used in treatment of AIDS, at 100 μg/ml, purchased from Sigma, into 99 μl of solution A. A glassy carbon (GC) electrode with 3 mm was used to immobilize polypyrrole/anti-AZT probes by an electrochemical deposition with the precusor solution containing pyrrole and AZT. During the electrochemical deposition, a platinum foil with much larger surface area than that of the GC, and a Ag/AgCl electrode were used as row and column electrodes, respectively. CH 660 potentiostat was used to conduct cyclic voltammetry (CV) over –0.1 to 1.0 vs. Ag/AgCl for four cycles for electrochemical synthesis. The anti-AZT was entrapped in the polypyrrole film as the probe molecule to detect AZT, a low molecular weight protein molecule in solutions. After the polypyrrole/protein probe film deposited on the microelectrode surface and was rinsed with PBS solution, a Solartron Impedance Frequency Analyzer 1260 with Electrochemical Interface 1287 was used to measure the impedance, $Z_0$ of the GC electrode in PBS buffer. Solutions with concentrations of AZT from 10 μg/ml to 1 μg/ml in PBS were prepared by series dilution method. Polypyrrole/anti-AZT electrodes were submerged in 200 μl of solutions with different concentrations of AZT, respectively, for 1.0 hours. Then the electrodes were washed by PBS to remove unbound AZT and placed in PBS for impedance measurements.

The impedance change of $(R-R_0)/R_0$ vs. concentrations is shown in FIG. 7 as denoted. $[d(|Z-Z_0|)/d\log(f)]/[d|Z_0|/d\log(f)]$ values were calculated with step of 0.001 and shown in FIG. 7 as denoted. As illustrated, $[d(|Z-Z_0|)/d\log(f)]/[d|Z_0|/d\log(f)]$ is more sensitive than $(R-R_0)/R_0$ by almost 1 order of magnitude.

Alternatively, the sensitivity enhancement by adding an inductor onto the detection circuit can be conducted by introducing a virtual inductor to process the results obtained by conventional ac impedance measurements. For example, in most electrochemical sensors, the components in an equivalent circuit are resistance, the real part, and capacitance, the imaginary part. An additional imaginary part, the virtual inductor could introduced during processing and calculating the experimental data with the S/N amplification method described above.

Of course, the above described embodiments are intended to be illustrative only and in no way limiting. The described embodiments of carrying out the invention are susceptible to many modifications of form, arrangement of parts, details and order of operation. The invention, rather, is intended to encompass all such modification within its scope, as defined by the claims.

What is claimed is:

1. An addressable chip comprising:
   a substrate;
   a plurality of counter electrodes formed on said substrate;
   a plurality of reference electrodes, each one substantially encircling a respective counter electrode one of said plurality of counter electrodes in the same plane as its respective counter electrodes;
   a plurality of working electrodes, groups of said plurality of working electrodes encircling each of said plurality of reference electrodes and electrically isolated from said counter electrodes;
   pairs of said counter/working electrodes for interconnection with a voltage source, to generate a potential for detection of chem/biological probe and target molecule interaction proximate a pair of counter/working electrodes.

2. The chip of claim 1, wherein said substrate comprises a planar surface is formed of hydrophobic material.

3. The chip of claim 2, wherein said planar surface of said substrate is coated with a hydrophobic layer.

4. The chip of claim 1, wherein said working and counter electrodes are formed of at least one of platinum, gold, metal, carbon, carbides, nitrides, and conductive polymers.

5. The chip of claim 1, further comprising at least one wall isolating fluids proximate each of said counter electrodes from other ones of said counter electrodes.

6. The chip of claim 1, further comprising at least one trench isolating fluids proximate each of said counter electrodes from other ones of said counter electrodes.

7. The chip of claim 1, wherein said substrate is formed of at least one of plastic, ceramic, glass, rubber, fabric, printed circuit board, and silicon.

8. The chip of claim 1, further comprising a plurality of interconnects allowing independent measurement of current flow between each one of said counter electrodes and one of said working electrodes about said each one of said counter electrodes.

9. The chip of claim 8, wherein one working electrode about each of said counter electrodes is interconnected with one working electrode of each of said groups of working electrodes.

10. The chip of claim 1, wherein each of said counter electrodes is generally rectangular, square or circular in shape.

11. The chip of claim 1, further comprising a plurality of electrolyte pads, each covering one of said counter electrodes and its surrounding group of working electrodes.

12. The chip of claim 11, wherein said electrolyte pads are insoluble.

13. The chip of claim 11, wherein said electrolyte pads are formed of an electrolyte selected from the group consisting of polyethylene oxide, polyvinyl(alcohol), polyvinyl acetate, polyacrylamide, poly(vinylpyridine), polyethyleneimine and their combinations.

14. A test apparatus comprising the chip of claim 1; and a measuring device for measuring electrical characteristics at a selected pair of said counter/working electrodes, to analyse an analyte proximate said one of said plurality pair of counter/working electrodes.

15. The test apparatus of claim 14, further comprising at least one inductor interconnected between said measuring device and said pair of said counter/working electrodes.

16. The test apparatus of claim 14, wherein said measuring device measures the frequency response of said selected pair of said counter/working electrodes.

17. The test apparatus of claim 16, further comprising at least one electrolyte pad covering at least said selected pair of said counter/working electrodes.

18. The test apparatus of claim 17, wherein said electrolyte pad is formed of cross-linked hydrogel.

19. The test apparatus of claim 17, wherein said electrolyte pad is formed of polyacryamide.

20. The test apparatus of claim 14, wherein said measuring device measures variation in impedance of said selected pair of said counter/working electrodes near a resonant frequency of said selected pair of said counter/working electrodes.

21. The test apparatus of claim 14, wherein said measuring device comprises a variable frequency voltage source.

* * * * *